(12) United States Patent
MacEwan et al.

(10) Patent No.: US 10,370,582 B2
(45) Date of Patent: Aug. 6, 2019

(54) COMPOUNDS AND METHOD FOR ENHANCED OIL RECOVERY USING SULFUR SURFACTANTS

(71) Applicant: Ingevity South Carolina, LLC, North Charleston, SC (US)

(72) Inventors: Kimberley D. MacEwan, Mount Pleasant, SC (US); Reinaldo C. Navarrete, Houston, TX (US); Chao Yang, Mount Pleasant, SC (US)

(73) Assignee: INGEVITY SOUTH CAROLINA, LLC, North Charleston, SC (US)

( * ) Notice: Subject to any disclaimer, the term of this patent is extended or adjusted under 35 U.S.C. 154(b) by 590 days.

(21) Appl. No.: 14/774,568

(22) PCT Filed: Mar. 13, 2014

(86) PCT No.: PCT/US2014/025393
§ 371 (c)(1),
(2) Date: Sep. 10, 2015

(87) PCT Pub. No.: WO2014/151296
PCT Pub. Date: Sep. 25, 2014

(65) Prior Publication Data
US 2016/0024373 A1 Jan. 28, 2016

Related U.S. Application Data

(60) Provisional application No. 61/786,662, filed on Mar. 15, 2013.

(51) Int. Cl.
| | | |
|---|---|---|
| *C09K 8/584* | (2006.01) |
| *C07D 233/16* | (2006.01) |
| *C07D 207/40* | (2006.01) |
| *C07D 209/48* | (2006.01) |
| *C07D 209/56* | (2006.01) |
| *C07C 305/06* | (2006.01) |
| *C07D 233/06* | (2006.01) |
| *E21B 43/16* | (2006.01) |
| *E21B 47/00* | (2012.01) |

(52) U.S. Cl.
CPC .......... *C09K 8/584* (2013.01); *C07C 305/06* (2013.01); *C07D 207/40* (2013.01); *C07D 209/48* (2013.01); *C07D 209/56* (2013.01); *C07D 233/06* (2013.01); *C07D 233/16* (2013.01); *E21B 43/16* (2013.01); *E21B 47/00* (2013.01)

(58) Field of Classification Search
CPC ........................................... E21B 43/26
See application file for complete search history.

(56) References Cited

FOREIGN PATENT DOCUMENTS

| DE | 1901257 | * | 7/1970 | ............... C23F 11/00 |
| FR | 2028158 | * | 9/1970 | ............... C23F 14/00 |

* cited by examiner

*Primary Examiner* — William D Hutton, Jr.
*Assistant Examiner* — Avi T Skaist
(74) *Attorney, Agent, or Firm* — Bryan D. Zerhusen, Esq.; Cantor Colburn LLP

(57) ABSTRACT

A method of enhanced oil recovery wherein: (a) a flooding composition is delivered into a subterranean reservoir; (b) the flooding composition includes a sulfur surfactant; and (c) the fluid produced from the subterranean reservoir can also be analyzed to determine if the surfactant is present in the fluid. The surfactant preferably includes a sulfonate moiety or other sulfur-containing moiety. The presence of the surfactant in the fluid produced from the subterranean reservoir is preferably determined by X-ray fluorescence spectroscopy, HPLC-AES, or HPLC-ICP.

2 Claims, No Drawings

COMPOUNDS AND METHOD FOR ENHANCED OIL RECOVERY USING SULFUR SURFACTANTS

RELATED CASE

This application claims the benefit of U.S. Provisional Patent Application Ser. No. 61/786,662 filed on Mar. 15, 2013 and incorporates said provisional application by reference into this document as if fully set out at this point.

FIELD OF INVENTION

The present invention relates to compounds, compositions, and methods for enhanced oil recovery using novel surfactants and methods of detection.

BACKGROUND OF THE INVENTION

A need exists for improved reservoir flooding compositions, surfactants, and methods for enhanced oil recovery. In particular, a need exists for such improved compositions and surfactants which can be used to: (1) increase oil recovery from the reservoir; (2) reduce adsorption of the surfactant on the rock formation surface; (3) better analyze and understand the geology of the reservoir during trials, (4) detect and quantify the adsorption of the flooding surfactant on the formation rock; (5) understand other phenomena occurring in the reservoir during enhanced oil recovery; and (6) optimize final commercial flooding operations and other enhanced oil recovery procedures performed in the reservoir.

SUMMARY OF THE INVENTION

The present invention provides a composition, method, and compounds for enhanced oil recovery which satisfy the needs and alleviate the problems discussed above.

In one aspect, there is provided an inventive method of enhanced oil recovery from a subterranean reservoir comprising the step of delivering an inventive flooding composition into the subterranean reservoir, the flooding composition including a novel surfactant comprising at least one sulfonate moiety or other sulfur-containing moiety, or a combination thereof.

In another aspect, the inventive method can further comprise the step of analyzing a fluid produced from the subterranean reservoir to determine if the novel surfactant is present in the fluid. To determine the presence of the novel surfactant in the fluid produced from the subterranean reservoir, the fluid will preferably be analyzed by X-ray fluorescence spectroscopy, HPLC-AES (high performance liquid chromatography-atomic emission detection), or HPLC-ICP (high performance liquid chromatography-inductively coupled plasma).

Further aspects, features, and advantages of the present invention will be apparent to those of ordinary skill in the art upon reading the following Detailed Description of the Preferred Embodiments.

DETAILED DESCRIPTION OF THE PREFERRED EMBODIMENTS

The present invention provides novel surfactants for flooding compositions used in enhanced oil recovery from a subterranean reservoir. The inventive flooding composition includes one or more novel surfactant compounds. The inventive method comprises the step of delivering the flooding composition into the subterranean reservoir and can also comprise the further step of analyzing the fluid produced from the subterranean reservoir to determine if the novel surfactant is present in the produced fluid.

Examples of novel surfactant materials suitable for use in the inventive flooding composition include, but are not limited to, compounds having one or more sulfonate moieties, other detectable sulfur-containing moieties, or a combination thereof.

Examples of novel surfactant compounds preferred for use in the inventive flooding composition include, but are not limited to, surfactants which exhibit Winsor Type III phase behavior in the presence of a given oil and brine system. One such example of an inventive surfactant compound can be prepared in accordance with the following reaction formula:

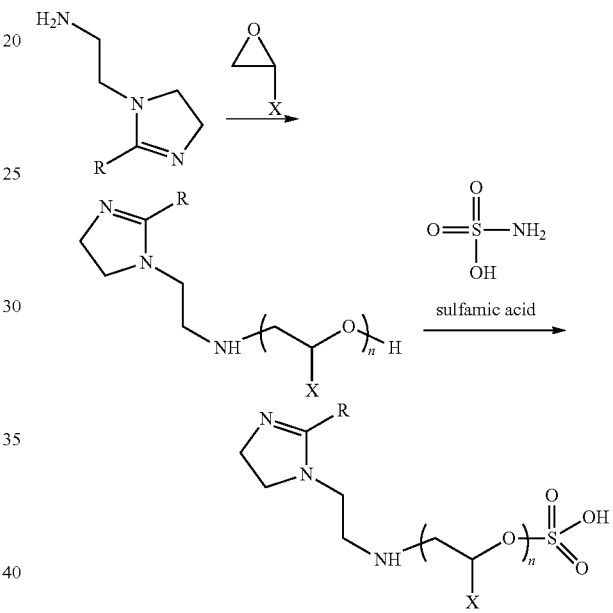

wherein: R will preferably be a linear or branched hydrocarbon constituent group having from about 8 to about 24 carbon atoms; X is hydrogen or a methyl group; and n is a value of from 1 to 12. In one embodiment, X is a methyl group and n is a value of from 1 to 5.

Further examples of inventive surfactant compounds can be prepared in accordance with the following reaction formula:

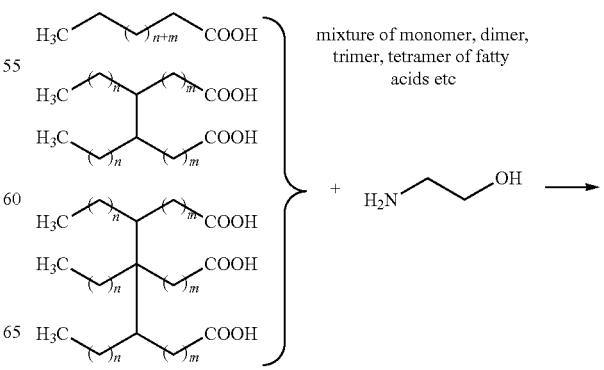

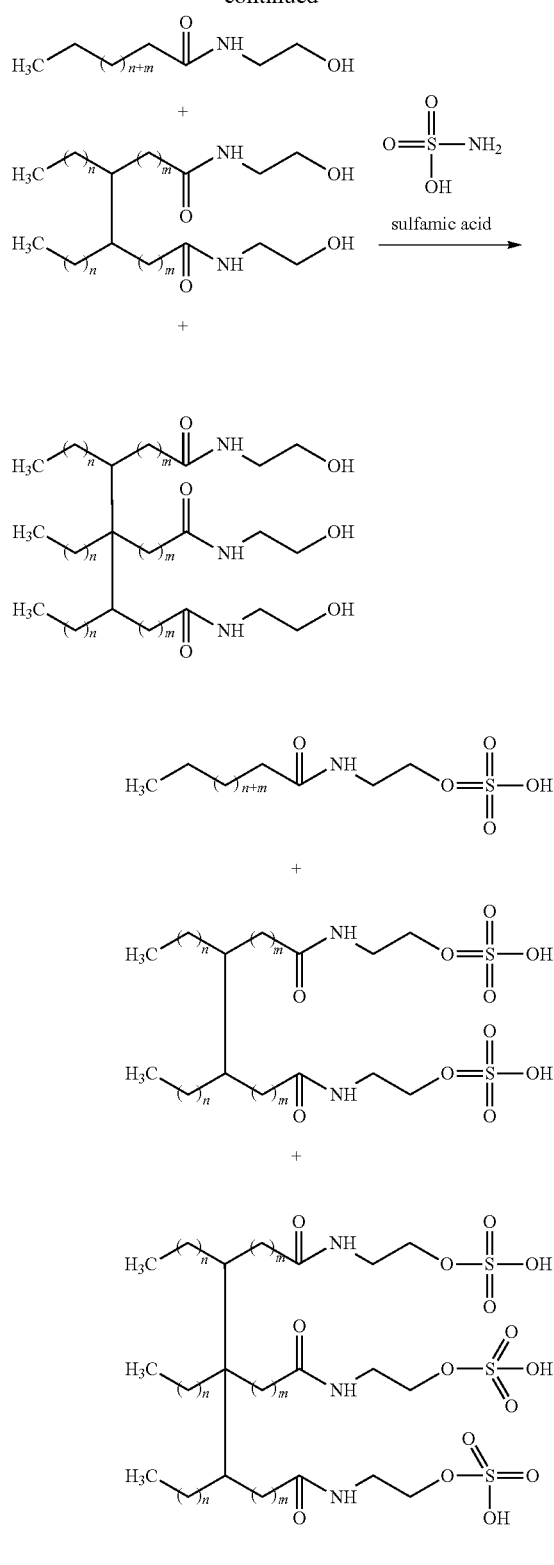

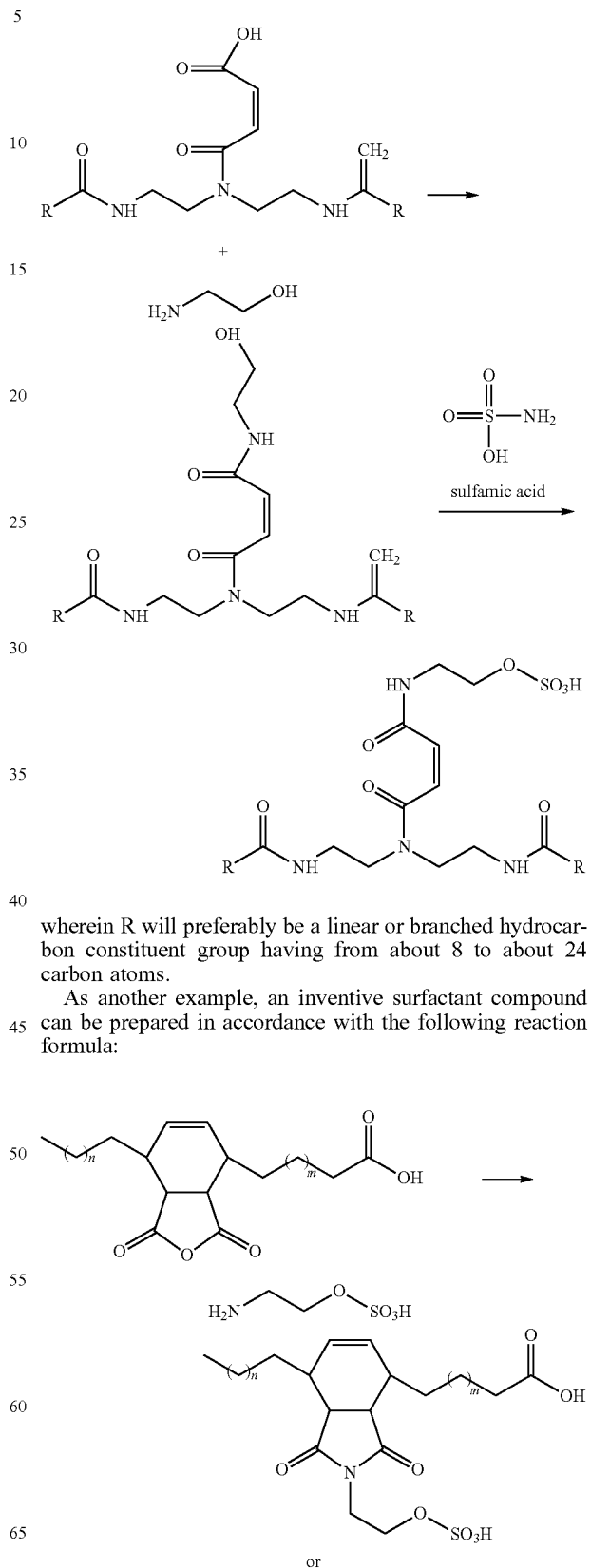

wherein the sum of n+m is preferably in the range of from about 10 to about 22 and wherein the fatty acid reactant or reactant mixture preferably comprises from about 50% to 100% by weight dimer molecules and from 0% to about 50% trimer molecules. This formula may also have the constituents linked together with cyclohexane rings.

Another example of an inventive surfactant compound can be prepared in accordance with the following reaction formula:

wherein R will preferably be a linear or branched hydrocarbon constituent group having from about 8 to about 24 carbon atoms.

As another example, an inventive surfactant compound can be prepared in accordance with the following reaction formula:

-continued

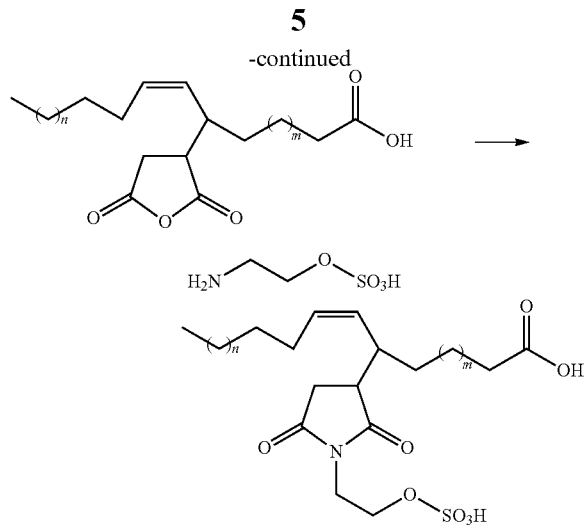

wherein n+m is a value of from 1 to 12.

As another example, an inventive surfactant compound can be prepared in accordance with the following reaction formula:

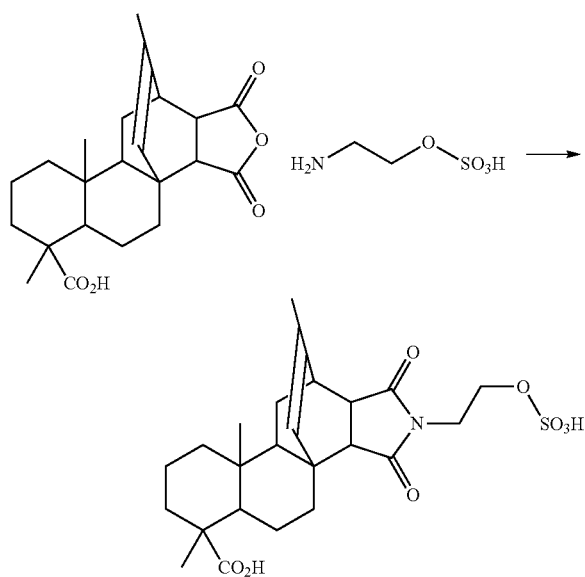

As another example, an inventive surfactant compound can be prepared in accordance with the following reaction formula:

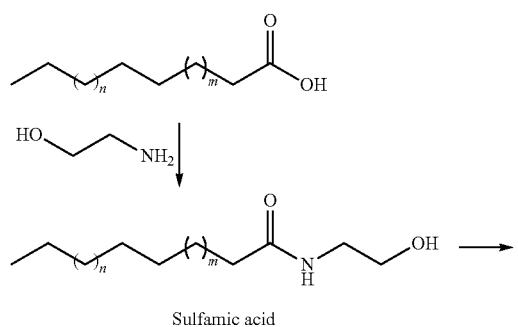

Sulfamic acid

-continued

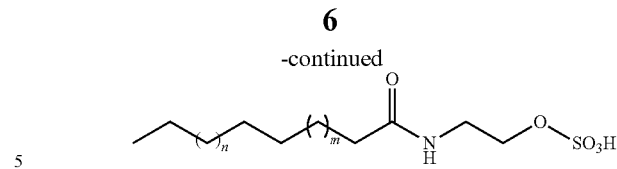

wherein n+m is a value of from 1 to 12.

As another example, an inventive surfactant compound can be prepared in accordance with the following reaction formula:

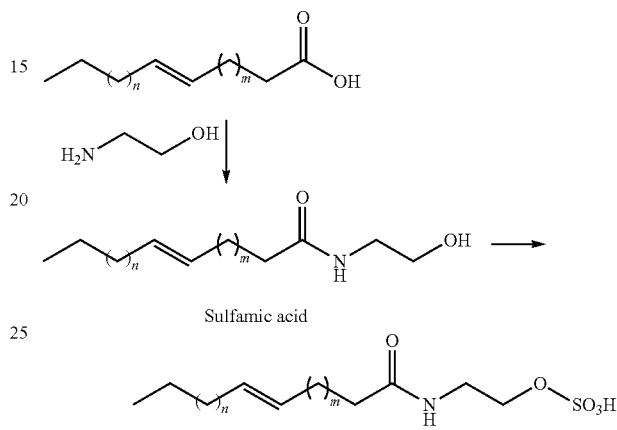

Sulfamic acid wherein n+m is a value of from 1 to 12.

As another example, an inventive surfactant compound can be prepared in accordance with the following reaction formula:

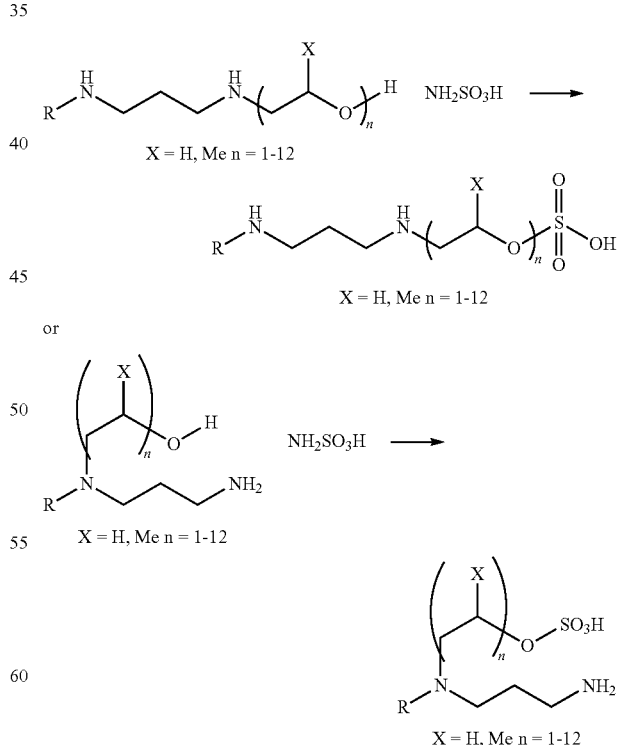

wherein: R is a linear or branched hydrocarbon constituent group having from 8 to 24 carbon atoms; X is hydrogen or a methyl group; and n is a value of from 1 to 12.

In addition, each of the formulas presented above can be further modified by using phosphoric acid, or by using other combinations of sulfur-containing and phosphorus-containing reactants to produce novel surfactants having both sulfur-containing moieties and phosphorus-containing moieties (e.g., phosphate, phosphonate, and/or phosphinate moieties).

The inventive flooding composition and method can be adapted for use in any type of reservoir flooding operation. One or more of the novel surfactants described above will preferably be present in the flooding composition in an amount in the range of from about 0.05% to about 2% by weight, based on the total weight of the flooding composition. The novel surfactants will typically be in liquid or powder form and will preferably be combined with a solvent (e.g., $C_4$ alcohol) when added to the flooding composition. The solvent will typically be present in an amount of from 0% to about 2% by weight based upon the total weight of the flooding composition and will also operate in the formation to lower the viscosity of the micro-emulsion which forms between the surfactant, oil and brine in the reservoir.

An example of one type of flooding operation which can be performed using the inventive flooding composition is a chemical enhanced oil recovery procedure wherein, in addition to including one or more novel surfactants as described above, the inventive flooding composition will further comprise (a) an aqueous brine solution which preferably is taylor made to provide optimal oil recovery with the formation brine salinity of the reservoir and (b) one or more polymers of the type commonly used in the art in flooding operations to provide mobility control so that the flood front will move uniformly through the reservoir, preferably without viscous fingering. For this type of enhanced oil recovery procedure, the novel surfactant(s) will preferably be present in the flooding composition in a total amount in the range of from about 0.5% to about 2% by weight and the polymer content of the flooding composition will preferably be in the range of from about 1000 to about 3000 ppm by weight.

As another example, the inventive method and flooding composition can also be used in alkaline/surfactant/polymer (ASP) flood type procedures wherein the oil in the reservoir has a high naphthenic acid content. The alkali in the flooding composition (e.g., sodium carbonate) reacts with the acid to produce fatty acid surfactant salts in situ. The production of these surfactant salts in situ reduces the amount of synthetic surfactant which must be added to the flooding composition. Consequently, in an operation of this type, the amount of novel surfactant added to the flooding composition will preferably be in the range of from about 0.05% to about 0.2% by weight.

When performing the additional second step of the inventive method of enhanced oil recovery wherein the fluid produced from the subterranean reservoir is analyzed to determine if the novel surfactant is present in the fluid, the sulfonate and/or other sulfur-containing moieties present in the surfactant structure allow the use of accurate analytical techniques, some of which can be readily implemented in the field. Examples of preferred analytical techniques include, but are not limited to X-ray fluorescence spectroscopy, HPLC-AES (high performance liquid chromatography—atomic emission detection), and HPLC-ICP (high performance liquid chromatography—inductively coupled plasma).

Using these analytical techniques, the operator is not only able to determine the presence of the novel surfactant(s) in the fluid produced from the reservoir, but can also determine the concentration of the surfactant(s) in the produced fluid over time.

Consequently, as noted above, the use of the inventive flooding composition and method allow the user to: (1) increase oil recovery from the reservoir; (2) lessen adsorption of the surfactant on rock formation surface; (3) better analyze and understand the geology of the reservoir during trials, etc.; (4) detect and quantify the adsorption of the flooding surfactant on the formation rock; (5) understand other phenomena occurring in the reservoir during enhanced oil recovery; and (6) optimize final commercial flooding operations and other enhanced oil recovery procedures performed in the reservoir.

In addition, the inventive flooding composition and method can also provide further important information regarding the structure and geology of the reservoir. For example, given that, in most cases, an injected flood front should advance through a reservoir at a rate of a few feet per day, if the surfactant arrives sooner than expected, then it is likely that a high permeability streak is present in the reservoir between the injection and production wells so that the flood is by-passing much of the oil remaining in the formation. On the other hand, if the surfactant takes too long to appear, then there may be too much adsorption of the surfactant on the formation rock, or the geology of the formation between the injection and production wells may be significantly different than expected.

Further, it will also be understood that the inventive method can optionally employ more than one detectable surfactant of the type described above which can be added to either the same injection well or to multiple injection wells. The use of more than one detectable surfactant can therefore be used, for example, to evaluate the relative adsorption characteristics of the different surfactants on the formation or rock and/or to obtain an even broader understanding of the overall geology of the reservoir.

The following Examples are intended to illustrate, but in no way limit, the invention as claimed.

Example 1

Preparation of Tallow Diamine Ethoxylate (m=10) Sulfonate Salt

Into a round bottomed flask equipped with reflux condenser, nitrogen inlet, temperature probe, and stirrer, there were charged 69.53 g of 10-mol-ethoxylate tallow diamine and 9.91 g of sulfamic acid. While introducing nitrogen into the flask, the temperature was slowly increased to 110° C. The reaction mixture was stirred for five hours at temperature 110-125° C. After the resulting mixture was cooled to 70° C., water was added. The reaction mixture was stirred for an additional two hours at this temperature before being cooled to room temperature and poured out.

Example 2

Preparation of Imidazoline Ethoxylate (m=8) Sulfonate Salt

Into a round bottomed flask equipped with reflux condenser, nitrogen inlet, temperature probe, and stirrer, there were charged 62.24 g of 8-mol-ethoxylate imidazoline and 8.03 g of sulfamic acid. While introducing nitrogen into the flask, the temperature was slowly increased to 110° C. The reaction mixture was stirred for four hours at a temperature of 110-135° C. After the resulting mixture was cooled to 70° C., water and isopropyl alcohol (IPA) were added. The reaction mixture was stirred for an additional two hours at this temperature before being cooled to room temperature and poured out.

Example 3

Preparation of Phosphoric Acid Tagged Tall Oil Fatty Acid (TOFA)

41.64 g of ethanol amine was heat to 50° C. under the nitrogen. 10.16 g of polyphosphoric acid (Aldrich) was added in. After addition, the reaction mixture was slowly heated to 100° C. and was allowed to proceed for four hours at 100° C.-120° C. After the resulting mixture was cooled to 80° C., IPA was added. The reaction mixture was stirred for another hour at this temperature before being cooled to room temperature. The reaction mixture was poured out.

Example 4

Preparation of Sulfonic Acid Tagged Tall Oil Fatty Acid

Into a round bottomed flask equipped with an addition funnel, nitrogen inlet, temperature probe, and stirrer, there were charged 148.17 g tall oil fatty acid and 98.67 g ethanol amine. While introducing nitrogen into the flask, the temperature was increased to 150° C. The mixture was stirred for three hours at this temperature. The reaction was monitored by FTIR. After the completion of the amide, the temperature was increased to 170° C. and excess of ethanol amine was removed. 68.13 g of the above amide was heated to 70° C. under nitrogen. 18.21 g of sulfamic acid was added in portions. After addition, the reaction mixture was allowed to proceed for three hours at 80° C. Water and IPA were added and the reaction mixture was stirred for another hour at this temperature before being cooled to room temperature and poured out.

Example 5

Preparation of Sulfonic Acid Tagged Maleated Tall Oil Fatty Acid

Into a round bottomed flask equipped with an addition funnel, nitrogen inlet, temperature probe, and stirrer, there were charged 61.71 g ethanol amine. While introducing nitrogen into the flask, 94.82 g of sulfamic acid was added in portions. After the addition, the temperature was increased to 80° C. The mixture was stirred for three hours at this temperature. After the reaction was complete, the reaction was quenched by a trace amount of water and cooled to room temperature. 25.01 g of the above amino ethylene sulfonic acid was dissolved in 60 ml de-ioned water and the PH was adjusted to 11 by NaOH. 38.21 g of maleated TOFA was added in portions. After addition, the reaction mixture was allowed to proceed for three hours at 80° C. Water and IPA were added and the reaction mixture was stirred for another hour at this temperature before being cooled to room temperature and poured out.

Example 6

Winsor III Screening Test Procedure

Aqueous solutions of NaCl in concentrations of 0.1-15 wt. percent were prepared with deionized water. Various surfactant solutions of appropriate HLB numbers were prepared from concentrations of 0.5-2.0 wt. percent in NaCl brines. Into clean and dry 10 mL scintillation vials was injected Sigma Aldrich HPLC grade 1.5 mL of dodecane. As is common in lab simulation procedures, the dodecane was used to simulate crude oil. Using a separate syringe, 1.5 mL of surfactant solutions were injected into the scintillation vials and the vials were capped. The vials were stirred vigorously using a vortex mixer for 10 seconds. The vials were allowed to sit undisturbed at room temperature and the presence or absence of a Winsor III phase was observed after 16 hours of equilibration.

Each of the surfactant solutions produced a Windsor III microemulsion phase, thereby displaying minimum surface tension performance desirable for displacement in enhanced oil recovery procedures. Table 1 lists the conditions at which the Winsor III behavior occurred.

TABLE 1

| | Conditions for forming Winsor Type III Systems | | | | | |
|---|---|---|---|---|---|---|
| | Primary Surfactant | Primary Surfactant Concentration (wt. %) | Cosurfactant | Cosurfactant Concentration | Total surfactant concentration | NaCl Brine concentration |
| 1 | Tallow diamine ethoxylate (10) sulfonate salt | 0.25-0.50% | Phosphate-tagged TOFA | 0.25-0.50% | 0.5-1.0% | 0% |
| 2 | Imidazoline ethoxylate (8) sulfonate salt | 0.60% | Sulfonate-tagged TOFA | 0.40% | 1% | 15% |

Example 7

ICP Detection of Tagged Surfactants

Sulfur ICP (Inductively Coupled Plasma) standards were made gravimetrically using a stock 1000 ppm sulfur standard and diluting with deionized water with less than 1% error. The 1000 ppm calibration standard was a stock sulfur solution. Seven calibration standards (25, 50, 100, 300, 600, 800, and 1000 ppm) were run on an Agilent 715 radial ICP-OES at 182.562 nm wavelength in triplicate using the Polyboost and Snoutpurge analysis mode. The average value was reported as the standard concentration within the instrument acceptable 20% error, yielding a calibration correlation coefficient of 0.999889. Following the calibration, three check standards: 25 ppm, 300 ppm, and 1000 ppm, were run with results of 24.4832 ppm, 304.298 ppm, and 1018.61 ppm respectively; all within instrument acceptable 20% error.

Samples were prepared by diluting with deionized water to approximately the middle of the calibration range. Each sample was run in triplicate with the average concentration being reported in ppm. As Table 2 shows, the surfactant concentration could be calculated from the tag with minimal error.

TABLE 2

Detectability of tagged surfactants

| Sample | Actual concentration (ppm) | Measured concentration (ppm) | Error (%) |
|---|---|---|---|
| Tallow diamine ethoxylate (10) sulfonate salt | 119.3 | 116.0 | 2.7 |
| Imidazoline ethoxylate (8) sulfonate salt | 267.8 | 274.8 | −2.6 |

Thus, the present invention is well adapted to carry out the objectives and attain the ends and advantages mentioned above as well as those inherent therein. While presently preferred embodiments have been described for purposes of this disclosure, numerous changes and modifications will be apparent to those of ordinary skill in the art. Such changes and modifications are encompassed within this invention as defined by the claims.

What is claimed is:

1. A compound of a formula:

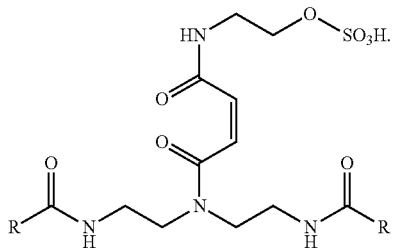

wherein R is a linear or branched hydrocarbon constituent group having from 8 to 24 carbon atoms.

2. A method of enhanced oil recovery from a subterranean reservoir comprising the:
   (a) delivering a flooding composition into said subterranean reservoir, said flooding composition including a surfactant comprising at least one sulfonate moiety or other sulfur-containing moiety, or a combination thereof; and
   (b) analyzing a fluid produced from said subterranean reservoir to determine if said surfactant is present in said fluid,
   wherein said surfactant comprises one or more compounds having a formula:

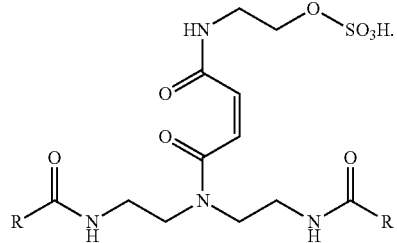

wherein R is a linear or branched hydrocarbon constituent group of having from 8 to 24 carbon atoms.

* * * * *